(12) United States Patent
Kühn

(10) Patent No.: US 7,727,369 B2
(45) Date of Patent: Jun. 1, 2010

(54) GAS SENSOR

(75) Inventor: Uwe Kühn, Wesenberg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 652 days.

(21) Appl. No.: 11/278,742

(22) Filed: Apr. 5, 2006

(65) Prior Publication Data

US 2006/0278527 A1 Dec. 14, 2006

(30) Foreign Application Priority Data

Jun. 8, 2005 (DE) .................. 10 2005 026 306

(51) Int. Cl.
*G01N 27/407* (2006.01)

(52) U.S. Cl. .................. 204/424; 204/426; 204/431

(58) Field of Classification Search ............ 204/424, 204/412, 425, 426, 427, 428, 429, 401
See application file for complete search history.

(56) References Cited

U.S. PATENT DOCUMENTS

| 4,132,616 | A | * | 1/1979 | Tantram et al. ............. 204/415 |
| 4,440,726 | A | | 4/1984 | Coulson |
| 4,472,247 | A | * | 9/1984 | Rohr et al. ............... 205/784.5 |
| 5,759,368 | A | * | 6/1998 | Kuhn ................... 204/403.01 |
| 6,284,112 | B1 | * | 9/2001 | Kato et al. ................ 204/425 |
| 6,325,906 | B1 | * | 12/2001 | Kitanoya et al. ........... 204/425 |
| 6,436,277 | B2 | * | 8/2002 | Schnaibel et al. .......... 205/784 |
| 2002/0121438 | A1 | * | 9/2002 | Saffell et al. ............... 204/415 |
| 2003/0155237 | A1 | | 8/2003 | Surridge et al. |

FOREIGN PATENT DOCUMENTS

| DE | 9421458 | 4/1996 |
| DE | 19547150 C2 | 6/1997 |
| EP | 0408039 | 1/1991 |
| GB | 2283321 | 5/1995 |
| WO | WO 03/032411 | 4/2003 |
| WO | WO 03/044511 | 5/2003 |
| WO | WO 2004/031758 | 4/2004 |
| WO | WO 2005/015195 | 2/2005 |
| WO | WO 2005/017516 | 2/2005 |

\* cited by examiner

*Primary Examiner*—Nam X Nguyen
*Assistant Examiner*—Jennifer Dieterle
(74) *Attorney, Agent, or Firm*—McGlew and Tuttle, P.C.

(57) ABSTRACT

A gas sensor is provided that has the diffusion of the measuring gas toward the working electrode adapted in such a way as to obtain a good signal-to-basic current ratio. Provisions are made for the measuring gas to be transported via a capillary arrangement (11), wherein the capillary arrangement (11) is designed as an arrangement extending in parallel to the working electrode (4).

8 Claims, 1 Drawing Sheet

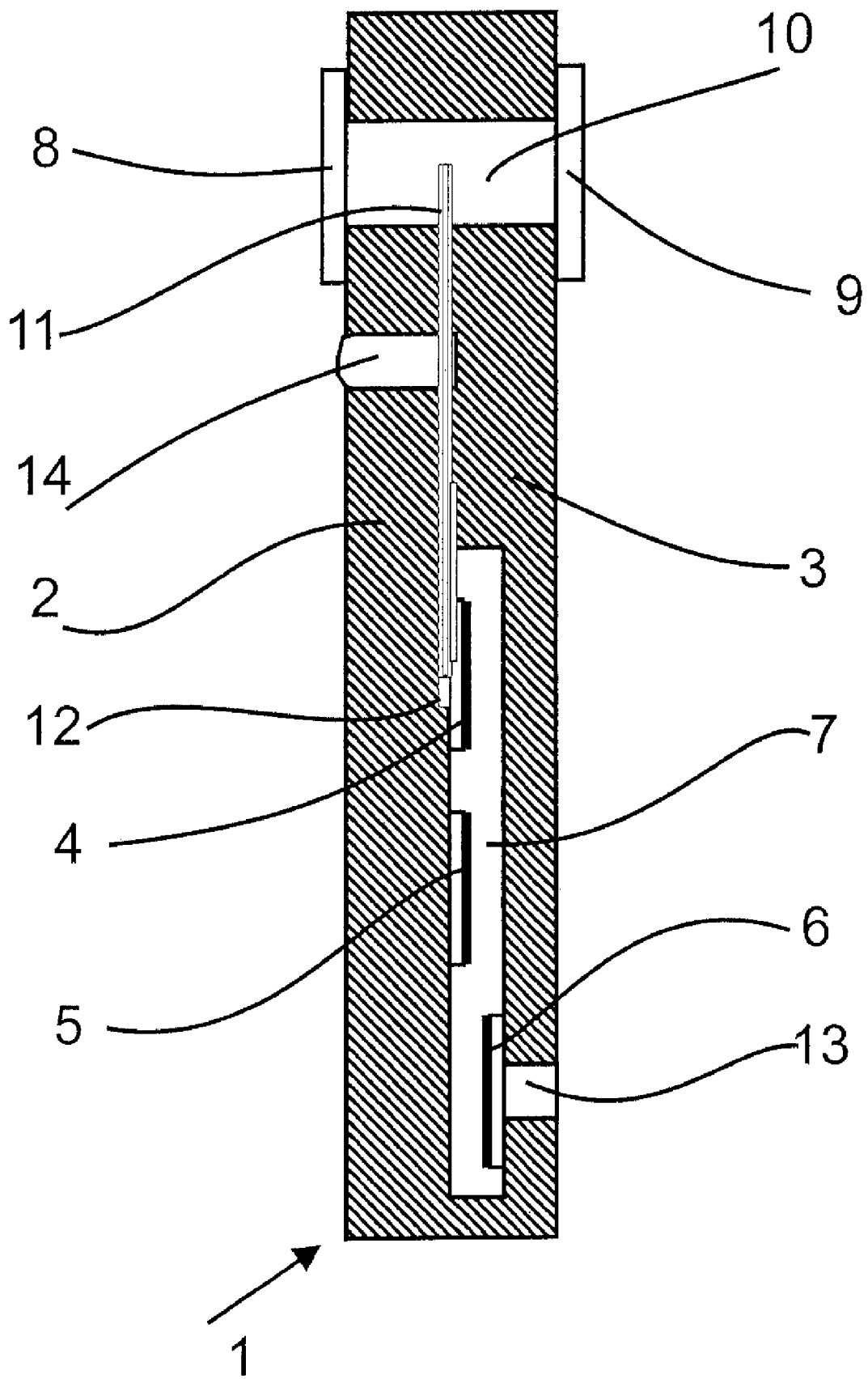

GAS SENSOR

CROSS REFERENCE TO RELATED APPLICATIONS

This application claims the benefit of priority under 35 U.S.C. §119 of German Patent Application DE 10 2005 026 306.2 filed Jun. 8, 2005, the entire contents of which are incorporated herein by reference.

FIELD OF THE INVENTION

The present invention pertains to a gas sensor with a gas sensor, which has an electrochemical measuring cell with diffusion-limited entry of gas to a working electrode via a capillary arrangement.

BACKGROUND OF THE INVENTION

In amperometric oxygen sensors, which operate in marginal operation, the oxygen supply to the working electrode must be limited by suitable measures because oxygen is inherently present at relatively high concentrations. The reduction may be performed by means of capillaries, channel structures or porous material. The reduction of the oxygen transport is of significance especially in case of portable devices, because oxygen is permanently present and leads to a continuous flow of current in the measuring device, which shortens the service life of the oxygen supply being carried.

An oxygen sensor of the said type has become known from U.S. Pat. No. 4,132,616. The prior-art oxygen sensor contains a working electrode and a counterelectrode, which are accommodated in an electrolyte-filled sensor housing. The gas reaches the working electrode via a capillary, which reduces the measuring gas supply to the working electrode. The capillary is closed with a porous PTFE membrane toward the measuring gas atmosphere. The capillary extends at right angles to the plane of the working electrode and is accommodated in an end cap, which is attached to the sensor housing in the area of the working electrode. The capillary has a length of a few mm.

In gas sensors with round sensor housing, the capillary can usually be integrated without greater problems. However, the length of the capillary is often limited, because certain installation dimensions must not be exceeded, and the possibilities of varying the diameter-to-length ratio are often limited.

However, flat gas sensors of a film-like structure, in which the working electrode is exposed directly to the measuring gas atmosphere via an opening in the film, are known as well.

Such a gas sensor is shown, for example, in DE 195 47 150 C2. Due to the design, diffusion can be limited here only with porous films, and there are only lmited possibilities for affecting the porosity and the transport of substances toward the working electrode. This has a disadvantageous effect on the value and the quality of the measured signal.

SUMMARY OF THE INVENTION

The basic object of the present invention is to improve a gas sensor of the type such that the diffusion of the measuring gas to the working electrode can be adapted in such a way as to obtain a good signal-to-current ratio.

According to the invention, a gas sensor is provided comprising an electrochemical measuring cell having a diffusion-limited gas entrance. A working electrode is provided with the sensor as well as a capillary arrangement. The measuring gas to be analyzed reaches the working electrode through the capillary arrangement. The capillary arrangement extends in parallel to the working electrode at least in some sections.

According to another aspect of the invention, a gas sensor is provided comprising a sensor housing defining a gas entrance, a gas collection space and a gas distribution space. A working electrode is disposed in communication with the gas distribution space. The working electrode is supported by the sensor housing with a working electrode disposition providing a portion extending in a plane. A capillary arrangement is provided for delivering the measuring gas to be analyzed from the gas collection space to the working electrode through the capillary arrangement. The capillary arrangement has a portion extending in parallel to the plane or along the plane at least in some sections.

The advantage of the present invention is essentially that a broader range of length-to-diameter ratios can be obtained with the capillary arrangement led in parallel to the working electrode over a certain section. An optimal signal-to-basic current ratio can thus be set without deterioration of the response time of the gas sensor. The capillary, arranged in the same plane, can be attached without problems especially in planar gas sensors, in which the working electrode and the counterelectrode are arranged in one plane, because the external dimensions of the electrode support remain unchanged and the overall length of the electrode support is available for the capillary. Many combinations of capillary lengths and diameters can thus be embodied without the need to take into account installation conditions.

However, the capillary arrangement according to the present invention can also be embodied in usual gas sensors with round sensor housing, in which case the entire length of the housing can be used for the capillary. The capillary may advantageously be made of glass or metal, but preferably plastic. The capillary does not have to extend along the length of the housing, but may also be designed as a coil, which is especially advantageous for round housing shapes. The power consumption of the gas sensor can be reduced to about 10% of that of current oxygen sensors due to the capillary arrangement according to the present invention.

The capillary arrangement is advantageously accommodated between two housing halves in the case of a sensor housing of planar design. The capillary arrangement is advantageously located in one plane with the working electrode and the reference electrode and is either welded in, incorporated by lamination or inserted between the housing halves. To seal the capillary arrangement within the sensor housing, it is advantageous to provide an opening in one housing half in the area in which the capillary extends and to bond the capillary arrangement to the sensor housing with a filled-in sealing compound.

A gas distribution space is preferably provided in the area of opening of the capillary arrangement in the area of the working electrode. It is achieved as a result that the measuring gas having entered by diffusion can be distributed uniformly over the area of the working electrode.

The capillary arrangement is closed with a porous, hydrophobic filter toward the gas atmosphere.

The capillary arrangement may consist of an individual capillary or a bundle of individual capillaries. The length of an individual capillary is advantageously in a range of 0.5 cm to 2 cm and the diameter is in a range of 20 µm to 150 µm.

An exemplary embodiment of the present invention is shown in the FIGURE and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a sectional view schematically illustrating an electrochemical measuring cell of planar design.

DESCRIPTION OF THE PREFERRED EMBODIMENTS

Referring to the drawings in particular, the only FIGURE schematically illustrates an electrochemical measuring cell 1 of planar design with a sensor housing comprising two housing halves 2, 3. A working electrode 4 and a reference electrode 5 are arranged on or at the first side housing part or left side housing half 2 and a counterelectrode 6 is arranged on or at the second side housing part or right side housing half 3. A nonwoven material 7 is impregnated with electrolyte. The nonwoven material 7 is located between the electrodes 4, 5, 6. The electrochemical measuring cell 1 has a diffusion-limited gas entrance with porous filters 8, 9. The measuring gas to be analyzed reaches a collection space 10 via the porous filters 8, 9 and a gas distribution space 12 in front of the working electrode 4 through a capillary 11. The capillary 11 extends between the housing halves 2, 3 in the plane formed by the working electrode 4 and the reference electrode 5. The housing parts 2 and 3 have opposed interior surfaces extending between said gas collection space 10 and said gas distribution space 12 and said capillary 11 extends along the sensor housing interior surfaces. The capillary 11 consists of plastic and has a length of 1.5 cm and a diameter of 50 µm. The electrochemical measuring cell 1 is designed for the detection of oxygen and operates according to the principle of a so-called "oxygen pump."

The measuring gas diffuses via the filters 8, 9 and the capillary 11 to the working electrode 4 and the oxygen content is electrochemically reacted at the electrode 4. The oxygen produced at the counterelectrode 6 is released into the environment via an opening 13. During the mounting of the electrochemical measuring cell 1, the capillary 11 is fixed at first only approximately between the housing halves 2, 3, so that it intersects a hole 14, which extends through the wall of the left housing half 2. The hole 14 is subsequently filled with epoxy resin. The capillary 11 is thus sealingly connected with the housing halves 2, 3.

The capillary 11 protrudes into the collection space 10 and the direction of opening can be determined by bending. The oxygen transport to the working electrode 4 can be optimized by shortening the capillary 11.

While specific embodiments of the invention have been shown and described in detail to illustrate the application of the principles of the invention, it will be understood that the invention may be embodied otherwise without departing from such principles.

What is claimed is:

1. A gas sensor comprising:
   a sensor housing comprising a first housing part and a second housing part together defining a gas entrance, a gas collection space and a gas distribution space, said first housing part having a first housing part interior surface extending between said gas collection space and said gas distribution space, said second housing part having a second housing part interior surface extending between said gas collection space and said gas distribution space, said first housing part interior surface being opposite said second housing part interior surface, one of said first housing part and said second housing part having a hole extending inwardly from an exterior of said housing and communicating with said first housing part interior surface and said second housing part interior surface;
   a diffusion-limiting barrier at said gas entrance whereby gas to be analyzed diffuses into said collection space through said diffusion-limiting barrier;
   a working electrode disposed in communication with said gas distribution space, said working electrode being supported by said sensor housing with a working electrode disposition providing a portion extending in a plane;
   a capillary tube arrangement between said first housing part interior surface and said second housing part interior surface with one end in said gas collection space and another end in said distribution space providing a gas diffusion path between said diffusion-limited gas entrance and said working electrode for diffusion of the measuring gas to be analyzed from said gas collection space to said working electrode through said capillary tube arrangement, said capillary tube arrangement having a portion extending in parallel to said plane or along said plane at least in some sections adjacent to said working electrode; and
   a sealing compound filling said hole for sealingly connecting said capillary tube arrangement with said first housing part and said second housing part.

2. A gas sensor in accordance with claim 1, wherein said sensor housing has a planar design.

3. A gas sensor in accordance with claim 2, wherein the capillary tube arrangement is welded in, incorporated by lamination or inserted in a contact plane with the working electrode.

4. A gas sensor in accordance with claim 1, wherein said gas distribution space is provided in an area of an opening of said capillary tube arrangement in the area of the working electrode.

5. A gas sensor in accordance with claim 1, wherein said diffusion-limiting barrier is a porous, hydrophobic filter and said capillary tube arrangement is closed toward the gas atmosphere at said gas entrance with said porous, hydrophobic filter.

6. A gas sensor in accordance with claim 1, wherein the capillary tube arrangement is formed of an individual capillary tube or a bundle of individual capillary tubes.

7. A gas sensor in accordance with claim 6, wherein the individual capillary tube has a length between 0.5 cm and 2 cm and a diameter between 20 µm and 150 µm.

8. A gas sensor in accordance with claim 1, further comprising:
   a counter electrode arranged in said plane and an electrolyte, said sensor housing further defining an electrolyte space with said electrolyte therein and with said working electrode in contact with said electrolyte and with said counter electrode in contact with said electrolyte and wherein said capillary tube arrangement includes a plurality of capillary tubes provided in parallel as a bundle, with each capillary tube having a diameter between 20 µm and 150 µm.

* * * * *